United States Patent [19]

Knüppel et al.

[11] Patent Number: 5,371,095
[45] Date of Patent: Dec. 6, 1994

[54] PYRIDYL COMPOUNDS WHICH HAVE PESTICIDAL ACTIVITY

[75] Inventors: Peter C. Knüppel, Wermelskirchen; Alexander Klausener, Cologne; Ralf Tiemann, Leverkusen; Stefan Dutzmann, Hilden; Heinz-Wilhelm Dehne; Ulrike Wachendorff-Neumann, both of Monheim, all of Germany

[73] Assignee: Bayer Aktiengesellschaft, Leverkusen, Germany

[21] Appl. No.: 58,651

[22] Filed: May 7, 1993

Related U.S. Application Data

[60] Continuation-in-part of Ser. No. 829,856, Jan. 31, 1992, Pat. No. 5,310,919, which is a division of Ser. No. 612,940, Nov. 13, 1990, Pat. No. 5,120,734, which is a division of Ser. No. 477,271, Jan. 8, 1990, Pat. No. 5,008,275.

[30] Foreign Application Priority Data

May 11, 1992 [DE] Germany ................ 4215469

[51] Int. Cl.$^5$ ............... C07D 213/74; A01N 43/40
[52] U.S. Cl. ................... 514/332; 514/352; 546/264; 546/312
[58] Field of Search ............ 546/255, 312, 264; 514/332, 352

[56] References Cited

U.S. PATENT DOCUMENTS

| 5,008,275 | 4/1991 | Klausener et al. ........... 546/334 |
| 5,120,734 | 6/1992 | Klausener et al. ........... 514/252 |

FOREIGN PATENT DOCUMENTS

| 0212859 | 3/1987 | European Pat. Off. ............ 514/252 |
| 0383117 | 2/1990 | European Pat. Off. ............ 546/255 |
| 0383117 | 8/1990 | European Pat. Off. ............ 514/252 |
| 3904931 | 8/1990 | Germany ............................ 546/255 |
| 2238308 | 5/1991 | United Kingdom ............... 514/252 |

Primary Examiner—C. Warren Ivy
Assistant Examiner—Zinna N. Davis
Attorney, Agent, or Firm—Sprung Horn Kramer & Woods

[57] ABSTRACT

There are described new pyridyl derivatives of the formula (I)

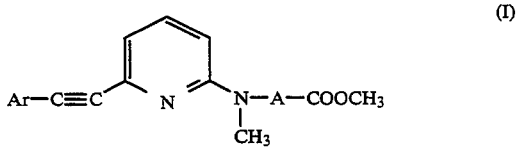

in which Ar and A have the meaning given in the description, their preparation, and new intermediates.

The new compounds of the formula (I) are used as pesticides.

6 Claims, No Drawings

PYRIDYL COMPOUNDS WHICH HAVE PESTICIDAL ACTIVITY

This is a continuation-in-part of application Ser. No. 07/829,856, filed on Jan. 31, 1992 now U.S. Pat. No. 5,310,919; which is a division of application Ser. No. 07/612,940, filed on Nov. 13, 1990, now U.S. Pat. No. 5,120,734; which is a division of application Ser. No. 07/477,271, filed on Jan. 8, 1990, now U.S. Pat. No. 5,008,275.

The invention relates to new pyridyl derivatives, to a plurality of processes for their preparation, and to their use as pesticides.

It is known that certain pyridyl-substituted acrylates such as, for example, the compound methyl 2-methoxy-1-{N-[6-(4-chlorophenyl-ethinyl)-2-pyridyl]-N-methyl}-aminoacrylate or the compound methyl 2-methoxy-1-{N-[6-(phenyl-ethinyl)-2-pyridyl]-N-methyl}-amino-acrylate, have fungicidal properties (compare, for example, EP 383,117).

However, the activity of these previously known compounds is not entirely satisfactory in all fields of application, in particular when low amounts and concentrations are applied.

New pyridyl derivatives of the general formula (I)

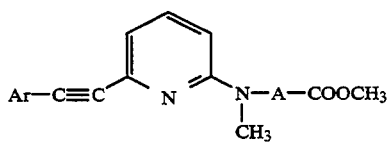

(I)

in which
Ar represents optionally substituted phenyl or optionally substituted pyridyl and
A represents a CH$_2$ group or a radical of the formula

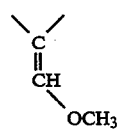

have been found, the compound methyl 2-methoxy-1-{N-[6-(4-chlorophenyl-ethinyl)-2-pyridyl]-N-methyl}-aminoacrylate, methyl 2-methoxy-1-{N-[6-(2-fluoro-4-chlorophenyl-ethinyl)-2-pyridyl)-N-methyl}-amino-acrylate, methyl 2-methoxy-1-{N-(4-fluoro-2-chlorophenyl-ethinyl)-2-pyridyl]-N-methyl}-amino-acrylate as well as the compound methyl 2-methoxy-1-{N-(6-phenyl-ethinyl)-2-pyridyl]-N-methyl}-amino-acrylate being excepted.

If appropriate, the compounds of the formula (I) can exist in the form of geometric and/or optical isomers or isomer mixtures of various compositions, depending on the nature of the substituents. The invention claims the pure isomers as well as the isomer mixtures.

Furthermore, it has been found that the new pyridyl derivatives of the general formula (I)

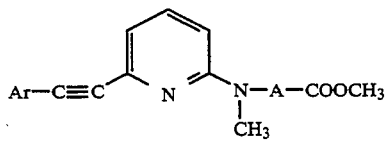

(I)

in which
Ar represents optionally substituted phenyl or optionally substituted pyridyl and
A represents a CH$_2$ group or a radical of the formula

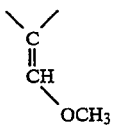

the compound methyl 2-methoxy-1-{N-[6-(4-chlorophenyl-ethinyl)-2-pyridyl]-N-methyl}-amino-acrylate, methyl 2-methoxy-1-{N-[6-(2-fluoro-4-chlorophenyl-ethinyl)-2-pyridyl]-N-methyl}-amino-acrylate, methyl 2-methoxy-1-{N-(4-fluoro-2-chlorophenyl-ethinyl)-2-pyridyl]-N-methyl}-amino-acrylate as well as the compound methyl 2-methoxy-1-{N-[6-(phenyl-ethinyl)-2-pyridyl]-N-methyl}-aminoacrylate being excepted, are obtained when a) phenylethinyl compounds of the formula (II)

$$Ar-C\equiv CH \quad \text{(II)}$$

in which
Ar has the abovementioned meaning,
are reacted with methyl N-(6-bromo-2-pyridyl)-sarcosinate, of the formula (III),

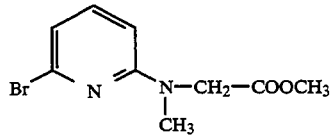

(III)

if appropriate in the presence of a diluent, if appropriate in the presence of a catalyst and if appropriate in the presence of a reaction auxiliary, or when b) methyl N-(6-ethinyl-2-pyridyl)-sarcosinate, of the formula (IV),

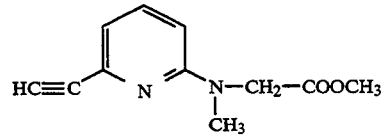

(IV)

is reacted with halogenoaromatics of the formula (V)

$$Ar-X \quad \text{(V)}$$

in which
X represents bromine or iodine and
Ar has the abovementioned meaning, if appropriate in the presence of a diluent, if appropriate in the presence of a catalyst and if appropriate in the presence of a reaction auxiliary, or when c) the pyridyl derivatives of the formula (Ia)

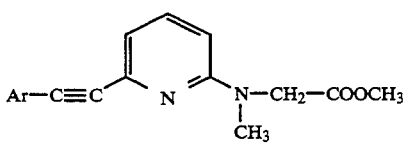

(Ia)

in which

Ar has the abovementioned meaning,
and which can be obtained with the aid of processes (a) or (b) according to the invention,
are reacted, in a subsequent reaction sequence, initially in a first step with orthoformic acid diamide esters of the formula (VI)

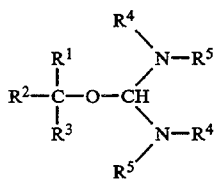

(VI)

in which $R^1$ represents hydrogen or alkyl, $R^2$ and $R^3$ either independently of one another in each case represent alkyl, or, together with the carbon atom to which they are bonded, represent a cycloalkyl radical, and $R^4$ and $R^5$ either independently of one another in each case represent alkyl, or, together with the nitrogen atom to which they are bonded, represent a heterocycle which can optionally contain further hetero atoms, if appropriate in the presence of a diluent, and the resulting amino acrylates of the formula (VII)

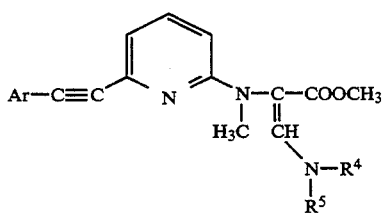

(VII)

in which

Ar, $R^4$ and $R^5$ have the abovementioned meaning,
are then, in a subsequent second step, first hydrolysed with dilute mineral acid, if appropriate in the presence of a diluent, and the resulting hydroxy acrylates of the formula (VIII)

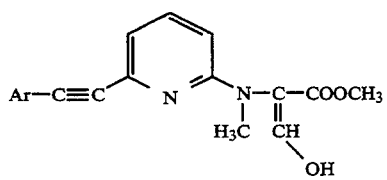

(VIII)

in which

Ar has the abovementioned meaning,
are then reacted, in a subsequent third step, with methylating agents, if appropriate in the presence of a diluent and if appropriate in the presence of a reaction auxiliary.

Finally, it has been found that the new pyridyl derivatives of the general formula (I) have a good activity against pests.

Surprisingly, the compounds of the general formula (I) according to the invention show a better fungicidal and acaricidal activity than the pyridyl-substituted acrylates which are known from the prior art and which are similar compounds chemically and from the point of view of their action.

Formula (I) provides a general definition of the pyridyl derivatives according to the invention. Preferred compounds of the formula (I) are those in which Ar represents phenyl or pyridyl, each of which is optionally monosubstituted or polysubstituted by identical or different substituents, suitable substituents in each case being:

halogen, cyano, nitro, in each case straight-chain or branched alkyl, alkoxy or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl or alkoximinoalkyl, each of which has 1 to 4 carbon atoms in the individual alkyl moieties, as well as phenyl which is optionally monosubstituted or polysubstituted by identical or different substituents from the series comprising halogen and/or straight-chain or branched alkyl having 1 to 4 carbon atoms, and A represents a $CH_2$ group or a radical of the formula

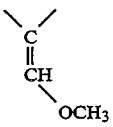

the compound methyl 2-methoxy-1-{N-[6-(4-chlorophenyl-ethinyl)-2-pyridyl]-N-methyl}-aminoacrylate, methyl 2-methoxy-1-{N-[6-(2-fluoro-4-chlorophenyl-ethinyl)-2-pyridyl]-N-methyl}-aminoacrylate, methyl 2-methoxy-1-{N-(4-fluoro-2-chlorophenyl-ethinyl)-2-pyridyl]-N-methyl} -aminoacrylate as well as the compound methyl 2-methoxy-1-{N-[6-(phenyl-ethinyl)-2-pyridyl]-N-methyl}-aminoacrylate being excepted.

Particularly preferred compounds of the formula (II) are those in which

Ar represents phenyl, 2-pyridyl, 3-pyridyl or 4-pyridyl, each of which is optionally monosubstituted to trisubstituted by identical or different substituents, suitable substituents in each case being:

halogen, cyano, nitro, in each case straight-chain or branched alkyl, alkoxy or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl or alkoximinoalkyl, each of which has 1 to 4 carbon atoms in the individual alkyl moieties, and A represents a $CH_2$ group or a radical of the formula

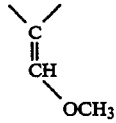

the compound methyl 2-methoxy-1-{N-[6-(4-chlorophenyl-ethinyl)- 2-pyridyl]-N-methyl}-aminoacrylate, methyl 2-methoxy-1-{N-[6-(2-fluoro-4-chlorophenyl-ethinyl)-2-pyridyl]-N-methyl}-aminoacrylate, methyl 2-methoxy-1-{N-(4-fluoro-2-chlorophenyl-ethinyl)-2-pyridyl]-N-methyl}-aminoacrylate as well as the compound methyl 2-methoxy-1-{N-[6-(phenyl-ethinyl)-2-pyridyl]-N-methyl}-aminoacrylate being excepted.

Very particularly preferred compounds of the formula (I) are those in which

Ar represents phenyl, 2-pyridyl or 4-pyridyl, each of which is optionally monosubstituted or disubstituted by identical or different substituents, suitable substituents in each case being:

fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, trifluoromethyl, trifluoromethoxy, trifluoromethylthio, methoxycarbonyl, ethoxycarbonyl, methoximinomethyl, methoximinoethyl, ethoximinomethyl or ethoximinoethyl, and A represents a $CH_2$ group or a radical of the formula

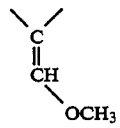

the compound methyl 2-methoxy-1-{N-[6-(4-chlorophenyl-ethinyl)-2-pyridyl]-N-methyl}-aminoacrylate, methyl 2-methoxy-1-{-N-[6-(2-fluoro-4-chlorophenyl-ethinyl)-2-pyridyl]-N-methyl}-aminoacrylate, methyl 2-methoxy-1-{N-(4-fluoro-2-chlorophenyl-ethinyl)-2-pyridyl]-N-methyl}-aminoacrylate as well as the compound methyl 2-methoxy-1-{N-[6-(phenyl-ethinyl)-2-pyridyl]-N-methyl}-aminoacrylate being excepted.

The compounds given in the preparation examples may be mentioned individually.

If, for example, methyl N-(6-bromo-2-pyridyl)-sarcosinate and 2-ethinyl-5-methoxy-chlorobenzene are used as starting substances, the course of the reaction of process (a) according to the invention can be represented by the following equation:

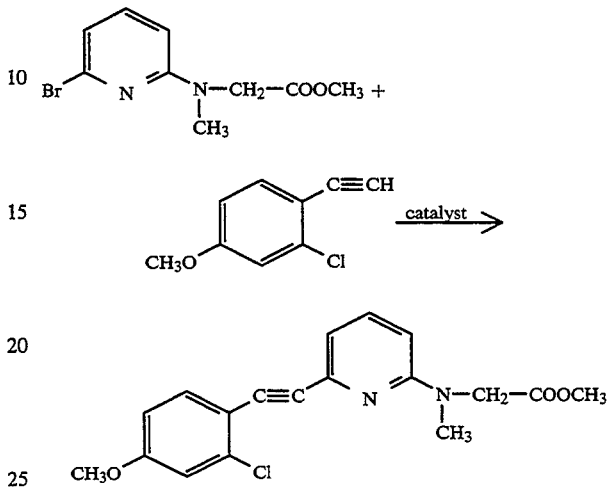

If, for example, methyl N-(6-ethinyl-2-pyridyl)-sarcosinate and 2,4-dichloro-iodobenzene are used as starting substances, the course of the reaction of process (b) according to the invention can be represented by the following equation:

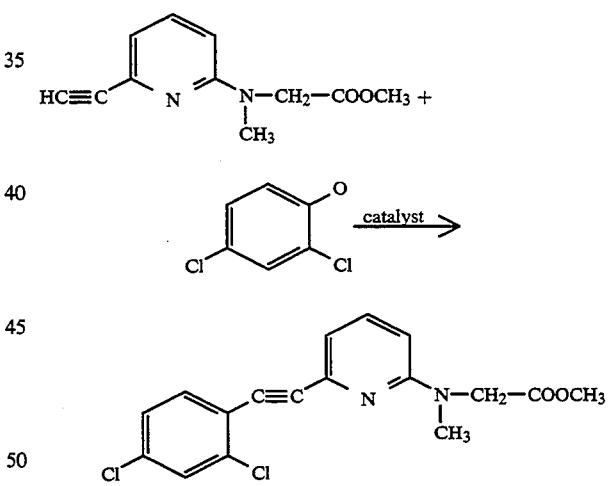

If, for example, methyl N-[6-(2-chloro-4-fluoro-phenylethinyl)-2-pyridinyl]-N-methyl-glycinate and t-butoxy-bis(dimethylamino)-methane are used as starting substances and dimethyl sulphate as the methylating agent, the course of the reaction of process (c) according to the invention can be represented by the following equation:

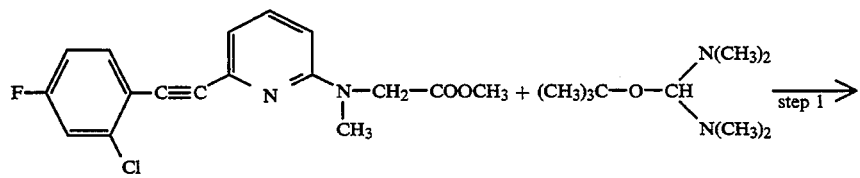

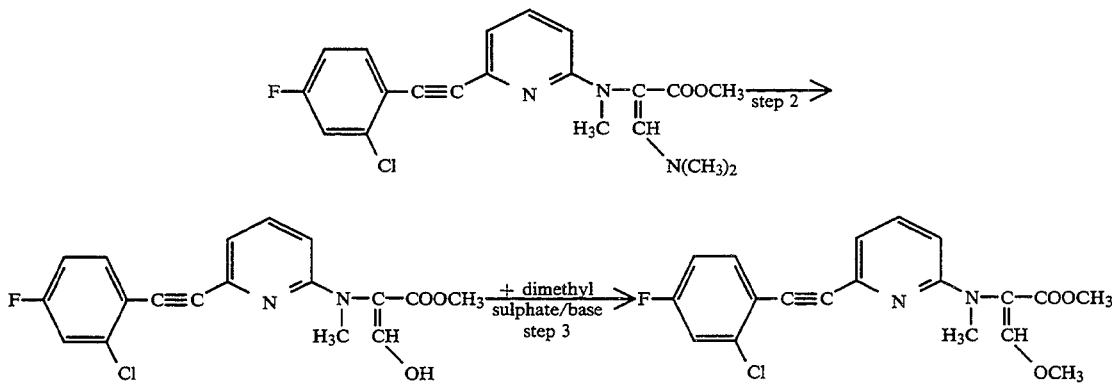

Formula (II) provides a general definition of the phenyl-ethinyl compounds required as starting substances for carrying out process (a) according to the invention. In this formula (II), Ar preferably represents those radicals which have already been mentioned in connection with the description of the compounds of the formula (I) according to the invention as being preferred for this substituent.

The phenylethinyl compounds of the formula (II) are known or can be obtained in analogy to known processes (compare, for example, J. Chem. Soc., Perkin Trans. I, 1985, 2443; Zh. Org. Khim. 16, 1893 [1980]; Synthesis 1983, 312; Synthesis 1981, 364; J. Org. Chem. 46, 2280 [1981]).

Methyl N-(6-bromo-2-pyridyl)-sarcosinate, of the formula (III), which is furthermore required as starting compound for carrying out process (a) according to the invention, has also been disclosed (compare, for example, DE 3,904,931).

Methyl N-(6-ethinyl-2-pyridyl)-sarcosinate, of the formula (IV), which is required as starting compound for carrying out process (b) according to the invention, was hitherto unknown and is also an object of the invention.

It is obtained when methyl N-(6-bromo-2-pyridyl)-sarcosinate, of the formula (III), is reacted with trimethylsilylacetylene in the presence of a diluent such as, for example, triethylamine and in the presence of a catalyst such as, for example, bis-(triphenylphosphine)-palladium(II) chloride/copper(I) chloride at temperatures between 20° and 150° C., if appropriate also under increased pressure, analogously to the procedure of processes (a) or (b) according to the invention, and the resulting compound methyl N-[6-(2-trimethylsilyl-ethinyl)-2-pyridyl]-sarcosinate, of the formula (IX)

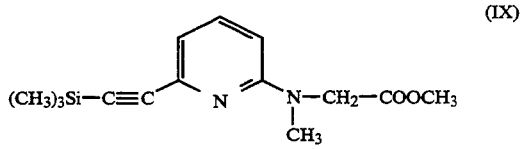

(IX)

is subsequently hydrolysed with bases such as, for example, potassium carbonate, in the presence of a diluent such as, for example, methanol, at temperatures between −20° C. and +60° C. (compare, in this context, also the preparation examples).

Methyl N-[6-(2-trimethylsilyl-ethinyl)-2-pyridyl]-sarcosinate, of the formula (IX), was hitherto unknown and is also an object of the invention.

Formula (V) provides a general definition of the halogenoaromatics furthermore required as starting substances for carrying out process (b) according to the invention. In this formula (V), Ar preferably represents those radicals which have already been mentioned in connection with the description of the compounds of the formula (I) according to the invention as being preferred for this substituent.

X preferably represents bromine or iodine.

The halogenoaromatics of the formula (V) are generally known compounds of organic chemistry.

Formula (Ia) provides a general definition of the pyridyl derivatives required as starting substances for carrying out process (c) according to the invention. In this formula (Ia), Ar preferably represents those radicals which have already been mentioned in connection with the description of the compounds of the formula (I) according to the invention as being preferred for this substituent.

The substituted pyridylpyrimidines of the formula (Ia) are compounds according to the invention and can be obtained with the aid of processes (a) or (b) according to the invention.

Formula (VI) provides a general definition of the orthoformic acid diamide esters furthermore required as starting substances for carrying out process (c) according to the invention. In this formula (VI), $R^1$, $R^2$, $R^3$, $R^4$ and $R^5$ preferably represent straight-chain or branched alkyl having 1 to 6 carbon atoms, in particular methyl, ethyl, n- or i-propyl as well as n-, i-, s- and t-butyl.

The orthoformic acid diamide esters of the formula (VI) are known (compare, for example, Chem. Ber. 101, 41–50 [1968]; Chem. Ber. 101, 1885–1888 [1968]; DE 2,303,919; PCT Int. Appl. WO 86/1204) or can be obtained in analogy to known processes.

The methylating agents furthermore required as starting substances for carrying out process (c) according to the invention are also generally known compounds of organic chemistry.

Suitable diluents for carrying out processes (a) and (b) according to the invention are inert organic solvents. These include, in particular, aliphatic, alicyclic or aromatic, optionally halogenated hydrocarbons such as, for example, benzine, benzene, toluene, xylene, chlorobenzene, dichlorobenzene, petroleum ether, hexane, cyclohexane, dichloromethane, chloroform or carbon tetrachloride; ethers such as diethyl ether, diisopropyl ether, dioxane, tetrahydrofuran or ethylene glycol dimethyl ether or ethylene glycol diethyl ether; ketones such as acetone or butanone or methyl isobutyl ketone, nitriles such as acetonitrile, propionitrile or benzonitrile; amides such as N,N-dimethylformamide, N,N-dimethylacetamide, N-methyl-formanilide, N-methylpyrrolidone or hexamethylphosphoric triamide, esters such as methyl acetate or ethyl acetate or tertiary amines such as triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU).

If appropriate, processes (a) and (b) according to the invention can also be carried out in a two-phase system such as, for example, water/toluene or water/dichloromethane, if appropriate in the presence of a phase transfer catalyst. Examples of such catalysts which may be mentioned are: tetrabutylammonium iodide, tetrabutylammonium bromide, tetrabutylammonium chloride, tributylmethylphosphonium bromide, trimethyl-$C_{13}/C_{15}$-alkylammonium chloride, trimethyl-$C_{13}/C_{15}$-alkylammonium bromide, dibenzyl-dimethylammonium methylsulphate, dimethyl-$C_{12}/C_{14}$-alkylbenzylammonium chloride, dimethyl-$C_{12}/C_{14}$-alkylbenzylammonium bromide, tetrabutylammonium hydroxide, triethylbenzylammonium chloride, methyltrioctylammonium chloride, trimethylbenzylammonium chloride, 15-crown-5, 18-crown-6 or tris-[2-(2-methoxyethoxy)ethyl]-amine.

Processes (a) and (b) according to the invention are preferably carried out in the presence of a suitable catalyst. Suitable catalysts are, in particular, palladium catalysts such as, for example, palladium chloride, palladium acetate, palladium sulphate, elemental palladium or palladium/phosphine complexes such as, for example, bis-(triphenylphosphine)-palladium(II) chloride, if appropriate on a suitable support such as, for example, active carbon or silicon dioxide, also in the presence of copper(I) salts such as, for example, copper iodide, copper chloride or copper bromide.

When carrying out processes (a) and (b) according to the invention, the reaction temperatures can be varied within a substantial range. In general, the process is carried out at temperatures between 0° C. and 150° C., preferably at temperatures between 50° C. and 120° C.

For carrying out process (a) according to the invention, 1.0 to 2.0 moles, preferably 1.0 to 1.2 moles, of methyl N-(6-bromo-2-pyridyl)-sarcosinate, of the formula (III), and 0.0001 to 0.5 mole, preferably 0.001 to 0.1 mole, of palladium catalyst as well as 0.0001 to 0.5 mole, preferably 0.001 to 0.1 mole, of copper(I) halide are generally employed per mole of phenylethinyl compound of the formula (II).

The reaction is carried out and the reaction products are worked up and isolated analogously to known processes (compare, in this context, for example Synthesis 1983, 312; Synthesis 1981, 364 or the preparation examples).

For carrying out process (b) according to the invention, 1.0 to 2.0 moles, preferably 1.0 to 1.2 moles, of halogenoaromatic of the formula (V) and 0.0001 to 0.5 mole, preferably 0.001 to 0.1 mole, of catalyst as well as 0.001 to 2.0 moles, preferably 0.01 to 1.0 mole, of phase transfer catalyst are generally employed per mole of methyl N-(6-ethinyl-2-pyridyl)-sarcosinate of the formula (IV).

The reaction is carried out and the reaction products are worked up and isolated analogously to known processes (compare, in this context, for example Synthesis 1983, 312; Synthesis 1981, 364 or the preparation examples).

Suitable diluents for carrying out the first step of process (c) according to the invention are inert organic solvents. These include, in particular, aliphatic, alicyclic or aromatic, optionally halogenated hydrocarbons such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; amides, such as N,N-dimethylformamide, N,N-dimethylacetamide, N-methylformanilide, N-methylpyrrolidone or hexamethylphosphoric triamide.

It is also possible to carry out the first step of process (c) according to the invention entirely without an addition of solvents.

When carrying out the first step of process (c) according to the invention, the reaction temperatures can be varied within a substantial range. In general, the process is carried out at temperatures between −35° C. and +150° C., preferably at temperatures between 0° C. and 120° C.

The first step of process (c) according to the invention can also be carried out under reduced or increased pressure, but is preferably carried out under atmospheric pressure.

If appropriate, it can also be expedient to use an inert gas atmosphere such as, for example, nitrogen or argon, in the first step of process (c) according to the invention. In general, however, it is possible to carry out the process according to the invention under an ordinary ambient atmosphere.

To carry out the first step of process (c) according to the invention, 1.0 to 15.0 moles, preferably 1.0 to 5.0 moles, of orthoformate of the formula (VI) are generally employed per mole of pyridyl derivative of the formula (Ia).

The reaction is carried out and the reaction products are worked up and isolated by known processes (compare, in this context, for example DE 4,025,892 or the preparation examples).

Suitable acids for carrying out the second step of process (c) according to the invention are conventional mineral acids. Acids which are preferably used for the hydrolysis of the enamines of the formula (VII) are dilute aqueous hydrochloric acid or sulphuric acid.

Suitable diluents for carrying out process (c) according to the invention are polar organic solvents or aqueous systems. These include, in particular, ethers, such as dioxane, tetrahydrofuran or ethylene glycol dimethyl ether or ethylene glycol diethyl ether; ketones, such as acetone; nitriles, such as acetonitrile; amides, such as N,N-dimethylformamide, N,N-dimethylacetamide, N-methylformanilide, N-methylpyrrolidone or hexamethylphosphoric triamide, or alcohols, such as methanol, ethanol, n- or i-propanol, their mixtures with water, or pure water.

When carrying out the second step of process (c) according to the invention, the reaction temperatures can be varied within a substantial range. In general, the process is carried out at temperatures between −20° C. and 100° C., preferably at temperatures between 0° C. and 60° C.

To carry out the second step of process (c) according to the invention, 1.0 to 5.0 moles, preferably 2.0 to 2.5 moles, of dilute aqueous acid are generally employed per mole of aminoacrylate of the formula (VII).

The reaction is carried out and the reaction products are worked up and isolated by known processes (compare, in this context, for example DE 4,025,892 or the preparation examples).

Suitable methylating agents for carrying out the third step of process (c) according to the invention are all customary methylating agents. Examples which may be mentioned in this context are methyl iodide, dimethyl sulphate or methyl tosylate.

Suitable diluents for carrying out the third step of process (c) according to the invention are also inert organic solvents. These include, in particular, aliphatic, alicyclic or aromatic, optionally halogenated hydrocarbons such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketone; nitriles, such as acetonitrile, propionitrile or benzonitrile; amides, such as N,N-dimethylformamide, N,N-dimethylacetamide, N-methylformanilide, N-methylpyrrolidone or hexamethylphosphoric triamide; esters such as methyl acetate or ethyl acetate or sulphoxides, such as dimethyl sulphoxide.

If appropriate, the third step of process (c) according to the invention can also be carried out in a two-phase system such as, for example, water/toluene or water/dichloromethane, if appropriate in the presence of a phase transfer catalyst. Examples of such catalysts which may be mentioned are: tetrabutylammonium iodide, tetrabutylammonium bromide, tetrabutylammonium chloride, tributylmethylphosphonium bromide, trimethyl-$C_{13}$/$C_{15}$-alkylammonium chloride, trimethyl-$C_{13}$/$C_{15}$-alkylammonium bromide, dibenzyl-dimethylammonium methylsulphate, dimethyl-$C_{12}$/$C_{14}$-alkyl-benzylammonium chloride, dimethyl-$C_{12}$/$C_{14}$-alkyl-benzylammonium bromide, tetrabutylammonium hydroxide, triethylbenzylammonium chloride, methyltrioctylammonium chloride, trimethylbenzylammonium chloride, 15-crown-5, 18-crown-6 or tris-[2-(2-methoxyethoxy)ethyl]-amine.

The third step of process (c) according to the invention is preferably carried out in the presence of a suitable reaction auxiliary. Suitable reaction auxiliaries are all conventional inorganic and organic bases.

These include, for example, hydrides, hydroxides, amides, alcoholates, acetates, carbonates or hydrogen carbonates of alkaline earth metals or alkali metals such as, for example, sodium hydride, sodium amide, sodium methylate, sodium ethylate, potassium tert-butylate, sodium hydroxide, potassium hydroxide, ammonium hydroxide, sodium acetate, potassium acetate, calcium acetate, ammonium acetate, sodium carbonate, potassium carbonate, potassium hydrogen carbonate, sodium hydrogen carbonate or ammonium carbonate as well as tertiary amines, such as trimethylamine, triethylamine, tributylamine, N,N-dimethylaniline, pyridine, piperidine, N-methylpiperidine, N,N-dimethylaminopyridine, diazabicyclooctane (DABCO), diazabicyclononene (DBN) or diazabicycloundecene (DBU).

When carrying out the third step of process (c) according to the invention, the reaction temperatures can be varied within a substantial range. In general, the process is carried out at temperatures between 0° C. and 150° C., preferably at temperatures between 20° C. and 100° C.

To carry out the third step of process (c) according to the invention, 1.0 to 10.0 moles, preferably 1.0 to 5.0 moles, of methylating agent and, if appropriate, 1.0 to 5.0 moles, preferably 1.0 to 2.5 moles, of reaction auxiliary are generally employed per mole of hydroxyacrylate of the formula (VIII).

The reaction is carried out and the reaction products are worked up and isolated by known processes. In a particular embodiment, it is also possible to carry out the second and third steps of process (c) according to the invention in one reaction step without isolating the intermediates of the formula (VIII), in a so-called "one-pot process" (compare also the preparation examples).

The end products of the formula (I) are purified with the aid of conventional processes, for example by column chromatography or by recrystallisation.

They are characterised with the aid of the melting point or, in the case of compounds which do not crystallise, with the aid of proton nuclear resonance spectroscopy ($^1$H NMR).

The active compounds according to the invention exhibit a powerful action against pests and can be employed in practice for combating undesired harmful organisms. The active compounds are suitable for use as plant protection agents, in particular as fungicides.

Fungicidal agents in plant protection are employed for combating *Plasmodiophoromycetes, Oomycetes, Chytridiomycetes, Zygomycetes, Ascomycetes, Basidiomycetes* and *Deuteromycetes*.

Some causative organisms of fungal diseases which come under the generic names listed above may be mentioned as examples, but not by way of limitation:

*Pythium* species, such as, for example, *Pythium ultimum;*

*Phytophthora* species, such as, for example, *Phytophthora infestans;*

*Pseudoperonospora* species, such as, for example, *Pseudoperonospora humuli* or *Pseudoperonospora cubensis;*

*Plasmopara* species, such as, for example, *Plasmopara viticola;*

*Peronospora* species, such as, for example, *Peronospora pisi* or *P. brassicae;*

*Erysiphe* species, such as, for example, *Erysiphe graminis;*

*Sphaerotheca* species, such as, for example, *Sphaerotheca fuliginea;*

*Podosphaera* species, such as, for example, *Podosphaera leucotricha;*

*Venturia* species, such as, for example, *Venturia inaequalis;*

*Pyrenophora* species, such as, for example, *Pyrenophora teres* or *P. graminea* (conidia form: Drechslera, syn: Helminthosporium);

*Cochliobolus* species, such as, for example, *Cochliobolus sativus* (conidia form: Drechslera, syn: Helminthosporium);

*Uromyces* species, such as, for example, *Uromyces appendiculatus;*

*Puccinia* species, such as, for example, *Puccinia recondita;*

*Tilletia* species, such as, for example, *Tilletia caries;*

*Ustilago* species, such as, for example, *Ustilago nuda* or *Ustilago avenae;*

*Pellicularia* species, such as, for example, *Pellicularia sasakii;*

*Pyricularia* species, such as, for example, *Pyricularia oryzae;*

*Fusarium* species, such as, for example, *Fusarium culmorum;*

*Botrytis* species, such as, for example, *Botrytis cinerea;*

*Septoria* species, such as, for example, *Septoria nodorum;*

*Leptosphaeria* species, such as, for example, *Leptosphaeria nodorum;*

*Cercospora* species, such as, for example, *Cercospora canescens;*

*Alternaria* species, such as, for example, *Alternaria brassicae* and

*Pseudocercosporella* species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

In this context, the active compounds according to the invention can be employed with particularly good success for combating cereal diseases such as, for example, against the causative organism of net blotch on barley (*Pyrenophora teres*) or against the causative organism of barley or wheat leaf spot (*Cochliobolus sativus*) or against the causative organism of glume blotch on wheat (*Leptosphaeria nodorum*) or against the causative organism of powdery mildew on wheat or barley (*Erysiphe graminis*) or for combating diseases in fruit and vegetable growing such as, for example, against the causative organism of apple scab (*Venturia inaequalis*) or against the causative organism of powdery mildew on grapevines (*Uncinula necator*) or for combating rice diseases such as, for example, against the causative organism of rice blast disease (*Pyricularia oryzae*) or agains the causative organism of rice stem blight (*Pellicularia sasakii*). In addition, the active compounds according to the invention have a broad in-vitro activity.

The compounds of the formulae (IV) and (IX) which have been described as intermediates also have fungicidal activity and are claimed as such.

Moreover, the active compounds are also suitable for combating animal pests, preferably arthropods and nematodes, in particular insects and arachnids, which occur in agriculture, in forests, in the protection of stored products and of materials, and in the hygiene sector. They are active against normally sensitive and resistant species and against all or individual development stages. The abovementioned pests include:

From the order of the *Isopoda,* for example, *Oniscus asellus, Armadillidium vulgare* and *Porcellio scaber.*

From the order of the *Diplopoda,* for example, *Blaniulus guttulatus.*

From the order of the *Chilopoda,* for example, *Geophilus carpophagus* and *Scutigera spec.*

From the order of the *Symphyla,* for example, *Scutigerella immaculata.*

From the order of the *Thysanura,* for example, *Lepisma saccharina.*

From the order of the *Collembola,* for example, *Onychiurus armatus.*

From the order of the *Orthoptera,* for example, *Blatta orientalis, Periplaneta americana, Leucophaea maderae, Blattella germanica, Acheta domesticus, Gryllotalpa* spp., *Locusta migratoria migratorioides, Melanoplus differentialis* and *Schistocerca gregaria.*

From the order of the *Dermaptera,* for example, *Forficula auricularia.*

From the order of the *Isoptera,* for example, *Reticulitermes* spp.

From the order of the *Anoplura,* for example, *Phylloxera vastatrix, Pemphigus* spp., *Pediculus humanus corporis, Haematopinus* spp. and *Linognathus* spp.

From the order of the *Mallophaga,* for example, *Trichodectes* spp. and *Damalinea* spp.

From the order of the *Thysanoptera,* for example, *Hercinothrips femoralis* and *Thrips tabaci.*

From the order of the *Heteroptera,* for example, *Eurygaster* spp., *Dysdercus intermedius, Piesma quadrata, Cimex lectularius, Rhodnius prolixus* and *Triatoma* spp.

From the order of the *Homoptera,* for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. *Psylla* spp.

From the order of the *Lepidoptera,* for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria* spp., *Bucculatrixo thurberiella, Phyllocnistis citrella, Agrotis* spp., *Euxoa* spp., *Feltia* spp., *Earias insulana, Heliothis* spp., *Laphygma exigua, Mamestra brassicae, Panolis flammea, Prodenia litura, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the *Coleoptera,* for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis* and *Costelytra zealandica.*

From the order of the *Hymenoptera,* for example, *Diprion* spp., *Hoplocampa* spp., *Lasius* spp., *Monomorium pharaonisn* and *Vespa* spp.

From the order of the *Diptera,* for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae* and *Tipula paludosa.*

From the order of the *Siphonaptera,* for example, *Xenopsylla cheopis* and *Ceratophyllus* spp.

From the order of the *Arachnida,* for example, *Scorpio maurus* and *Latrodectus mactans.*

From the order of the *Acarina,* for example, *Acarus siro, Argas* spp., *Ornithodoros* spp., *Dermanyssus gallinae, Eriophyes ribis, phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp. and *Tetranychus* spp.

The active compounds according to the invention are distinguished by a high acaricidal activity.

They can be employed with particularly good success for combating mites which are harmful to plants such as, for example, against the two-spotted spider mite (*Tetranychus urticae*). In addition, the active compounds according to the invention also have a leaf-acting insecticidal activity.

Depending on their particular physical and/or chemical properties, the active compounds can be converted into the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks: as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids can be used in the formulations. Other additives can be mineral and vegetable oils.

Colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and tin can be used.

The formulations in general contain between 0.1 and 95 per cent by weight of active compound, preferably between 0.5 and 90%.

When used as fungicides, the active compounds according to the invention can be present in the formulations as a mixture with other known active compounds, such as fungicides, insecticides, acaricides and herbicides, as well as in mixtures with fertilisers and growth regulators.

When used as fungicides, the active compounds can be used as such or in the form of their formulations or the use forms prepared therefrom, such as ready-to-use solutions, suspensions, wettable powders, pastes, soluble powders, dusting agents and granules. They are used in the customary manner, for example by watering, spraying, atomising, scattering, dusting, foaming, brushing on and the like. It is furthermore possible to apply the active compounds by the ultra-low-volume method or to inject the active compound preparation or the active compound itself into the soil. The seed of the plants can also be treated.

When the active compounds are used as fungicides in the use forms in the treatment of parts of plants, the active compound concentrations can be varied within a substantial range. They are generally between 1 and 0.0001% by weight, preferably between 0.5 and 0.001%.

When the active compounds are used as fungicides in the treatment of seed, amounts of 0.001 to 50 g of active compound, preferably 0.01 to 10 g, are generally required per kilogram of seed.

When the active compounds are used as fungicides in the treatment of soil, concentrations of 0.00001 to 0.1% by weight, preferably 0.0001 to 0.02%, of active compound are required at the site of action.

When used as insecticides and acaricides, the active compounds according to the invention can be present in their commercially available formulations and in the use forms prepared from these formulations as a mixture with other active compounds, such as insecticides, attractants, sterilants, acaricides, nematicides, fungicides, growth-regulating substances or herbicides. The insecticides include, for example, phosphoric acid esters, carbamates, carboxylic acid esters, chlorinated hydrocarbons, phenylureas, substances produced by microorganisms and the like.

When used as insecticides and acaricides, the active compounds according to the invention can furthermore be present in their commercially available formulations and in the use forms prepared from these formulations as a mixture with synergists. Synergists are compounds by which the action of the active compounds is increased without it being necessary for the synergist added to be active itself.

The active compound content of the use forms prepared from the commercially available formulations can vary within wide ranges. The active compound concentration of the use forms can be from 0.0000001 up to 95% by weight of active compound, preferably between 0.0001 and 1% by weight.

As insecticides and acaricides, they are used in a conventional manner adapted to suit the use forms.

The preparation and the use of the active compounds according to the invention can be seen from the examples which follow.

PREPARATION EXAMPLES

Example 1

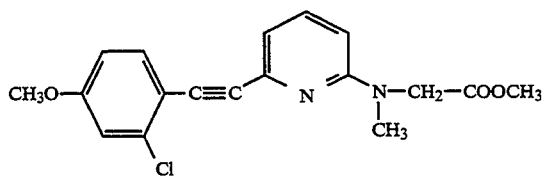

(Process a)

A mixture of 31.1 g (0.12 mol) of methyl N-(6-bromo-2-pyridyl)-sarcosinate, 20.0 g (0.12 mol) of 2-ethinyl-5-methoxy-chlorobenzene (compare, for example, J. Chem. Soc. Perkin Trans. I, 1985, 2443), 0.6 g (0.0085 mol) of bis-(triphenylphosphine)-palladium(II) chloride and 0.3 g (0.015 mol) of copper(I) iodide in 300 ml of triethylamine is refluxed for 4 hours, subsequently cooled to room temperature and filtered, the residue is washed with dichloromethane, the filtrate is concentrated in vacuo, and the residue is taken up in ethyl acetate, washed with water, dried over sodium sulphate, concentrated and chromatographed over silica gel (eluent: ethyl acetate/hexane 1:1).

25.1 g (61% of theory) of methyl N-{6-[2-(2-chloro-4-methoxyphenyl)-ethinyl]-2-pyridyl}-sarcosinate are obtained in the form of an oil.

$^1$H NMR (CDCl$_3$/tetramethylsilane): δ=3.73 (3H), 3.11 (3H), 4.43 (2H) ppm.

Example 2

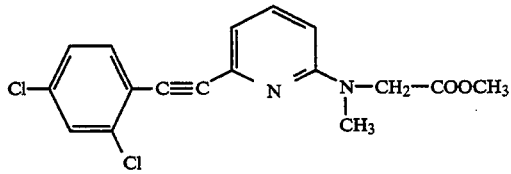

(Process b) 4.6 g (0.017 mol) of 1,3-dichloro-4-iodobenzene, 0.105 g (0.00015 mol) of bis-(triphenylphosphine)-palladium(II) chloride and 0.05 g (0.00026 mol) of copper(I) iodide are added in succession to 3.5 g (0.017 mol) of methyl N-(6-ethinyl-2-pyridyl)-sarcosinate in 50 ml of triethylamine, the mixture is stirred for 16 hours at 50° C., then cooled to room temperature, taken up in ethyl acetate, washed with water, dried over sodium sulphate and concentrated in vacuo, and the residue is purified by chromatography on silica gel (eluent: hexane/ethyl acetate 3:1).

3.7 g (62% of theory) of methyl N-{6-[2-(2,4-dichlorophenyl)-ethinyl]-2-pyridyl}-sarcosinate are obtained in the form of an oil.

$^1$H NMR (CDCl$_3$/tetramethylsilane): δ=3.73 (3H), 3.12 (3H), 4.42 (2H) ppm.

PREPARATION OF THE STARTING COMPOUND

Example IV

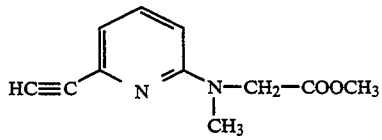

1.2 g (0.0087 mol) of potassium carbonate are added to 9.3 g (0.034 mol) of methyl N-[6-(2-trimethylsilyl-ethinyl)-2-pyridyl]-sarcosinate in 200 ml of methanol, and the mixture is subsequently stirred for 3 hours at room temperature. For working-up, the solvent is distilled off in vacuo, the residue is taken up in ethyl acetate, and the mixture is washed with water, dried over sodium sulphate and concentrated in vacuo. The residue is purified by chromatography on silica gel (eluent: hexane/ethyl acetate 1:1).

4.0 g (58% of theory) of methyl N-(6-ethinyl-2-pyridyl)-sarcosinate are obtained in the form of an oil.

$^1$H NMR (CDCl$_3$/tetramethylsilane): δ=3.72 (3H), 3.09 (3H), 4.40 (2H) ppm.

Example IX

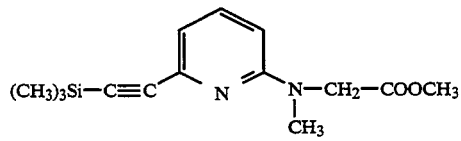

1.8 g (0.0026 mol) of bis-(triphenylphosphine)-palladium(II) chloride and 0.9 g (0.0047 mol) of copper(I) iodide are added to 15.5 g (0.06 mol) of methyl N-(6-bromo-2-pyridyl)-sarcosinate and 9 g (0.09 mol) of trimethylsilylacetylene in 60 ml of triethylamine, and the mixture is heated in a closed steel apparatus under the inherent pressure of the mixture which establishes itself for 16 hours at 90° C., subsequently cooled to room temperature and filtered, the residue is washed with diethyl ether, the filtrate is washed three times with water and dried over sodium sulphate, active charcoal is added, and the mixture is refiltered and concentrated in vacuo. The residue is purified by chromatography on silica gel (eluent: hexane/ethyl acetate 3:1).

9.3 g (56% of theory) of methyl N-[6-(2-trimethyl-silylethinyl)-2-pyridyl]-sarcosinate of melting point 85° C. to 86° C. are obtained.

Example 3

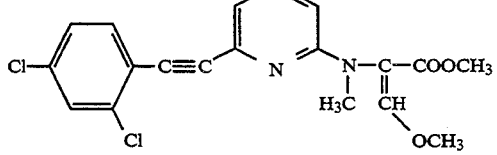

(Process c) 6.6 ml of 2N hydrochloric acid are added to 2.7 g (0.0066 mol) of methyl 2-{N-methyl-N-[6-(2,4-dichlorophenyl)-ethinyl-2-pyridyl]-amino}-3-dimethylaminoacrylate in 110 ml of acetone and 110 ml of water, and the mixture is subsequently stirred for 16 hours at room temperature. For working-up, the reaction mixture is treated with 1.32 g (0.016 mol) of sodium hydrogen carbonate, and the organic phase is separated off and concentrated in vacuo. The residue is taken up in 110 ml of dimethylformamide and treated with 2.2 g (0.017 mol) of dimethyl sulphate and 1.85 g (0.013 mol) of potassium carbonate, and the mixture is stirred for 16 hours at room temperature. For working-up, ethyl acetate and water are added, the organic phase is separated off, washed three times with water and dried over sodium sulphate, and the solvent is removed in vacuo. The residue is chromatographed over silica gel (eluent: hexane/ethyl acetate 1:3).

1.5 g (58% of theory) of methyl 2-{N-methyl-N-[6-(2,4-dichlorophenyl)-ethinyl-2-pyridyl]-amino}-3-methoxyacrylate are obtained in the form of an oil.

$^1$H NMR (CDCl$_3$/tetramethylsilane): $\delta = 3.70$ (3H), 3.24 (3H), 3.88 (3H) ppm.

PREPARATION OF THE STARTING COMPOUND

Example VII-1

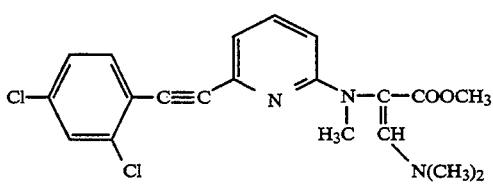

2.6 g (0.0074 mol) of methyl N-{6-[2-(2,4-dichlorophenyl)-ethinyl]-2-pyridyl}-sarcosinate are treated with 3.24 g (0.019 mol) of t-butoxy-bis-(dimethylamino)methane and the mixture is heated for three hours at 80° C. For working-up, the reaction mixture is treated with ethyl acetate and water, the organic phase is separated off and dried over sodium sulphate, and the solvent is removed in vacuo.

3.0 g (100% of theory) of methyl 2-{N-methyl-N-[6-(2,4-dichlorophenyl)-ethinyl-2-pyridyl]-amino}-3-dimethyl-amino-acrylate are obtained in the form of an oil.

$^1$H NMR (CDCl$_3$/tetramethylsilane): $\delta = 3.61$ (3H), 3.23 (3H), 2.95 (6H) ppm.

The following pyridyl-substituted acrylates of the general formula (I)

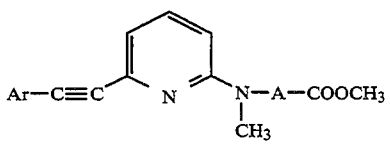

are obtained in a corresponding manner and in accordance with the general preparation instructions:

| Ex. No. | Ar | A | $^1$H NMR*) |
|---|---|---|---|
| 4 | 2-methylphenyl | —CH$_2$— | 3.73; 3.12; 4.46 |
| 5 | 2-pyridyl | —CH$_2$— | 3.73; 3.11; 4.45 |
| 6 | 2-methoxyphenyl | —CH$_2$— | 3.72; 3.10; 4.45 |
| 7 | 2-fluorophenyl | —CH$_2$— | 3.74; 3.11; 4.43 |
| 8 | 2-cyanophenyl | —CH$_2$— | 3.72; 3.12; 4.42 |
| 9 | 2,3-dichlorophenyl | —CH$_2$— | 3.73; 3.12; 4.42 |
| 10 | 3-chlorophenyl | —CH$_2$— | 3.74; 3.10; 4.40 |
| 11 | 2-chlorophenyl | —CH$_2$— | 3.73; 3.11; 4.42 |
| 12 | 2-methylphenyl | =C(COOCH$_3$)—CH=OCH$_3$ (implied) | 3.70; 3.25; 3.88 |

| Ex. No. | Ar | A | $^1$H NMR*) |
|---|---|---|---|
| 13 | 4-Cl, 3-F phenyl | C(=CHOCH$_3$)— | 3.70; 3.23; 3.50 |
| 14 | 4-F, 3-Cl phenyl | C(=CHOCH$_3$)— | 3.70; 3.24; 3.88 |
| 15 | 4-F$_3$CO phenyl | C(=CHOCH$_3$)— | 3.70; 3.24; 3.88 |
| 16 | 2-F phenyl | C(=CHOCH$_3$)— | 3.70; 3.24; 3.87 |
| 17 | 2-pyridyl | C(=CHOCH$_3$)— | 3.70; 3.24; 3.89 |
| 18 | 3-H$_3$CO, 4-Cl phenyl | C(=CHOCH$_3$)— | 3.70; 3.24; 3.88 |
| 19 | 2-OCH$_3$ phenyl | C(=CHOCH$_3$)— | 3.69; 3.24; 3.87 |
| 20 | 2-CN phenyl | C(=CHOCH$_3$)— | 3.71; 3.24; 3.89 |
| 21 | 2,3-diCl phenyl | C(=CHOCH$_3$)— | 3.70; 3.25; 3.88 |
| 22 | 3,4-diCl phenyl | C(=CHOCH$_3$)— | 3.70; 3.24; 3.88 |
| 23 | 2-Cl phenyl | C(=CHOCH$_3$)— | 3.70; 3.25; 3.88 |

*)The $^1$H NMR spectra were recorded in deuterochloroform (CDCl$_3$) or hexadeutero-dimethyl sulphoxide (DMSO-d$_6$) with tetramethylsilane (TMS) as the internal standard. The figures given are the chemical shift as δ value in ppm.

USE EXAMPLES

In the use examples which follow, the compounds listed below were employed as comparison substances:

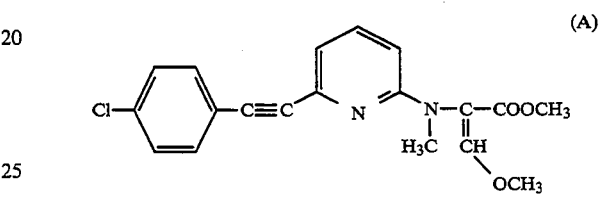

(A)

Methyl 2-methoxy-1-{N-[6-(4-chlorophenyl-ethinyl)-2-pyridyl]-N-methyl}-amino-acrylate (disclosed in EP 383,117)

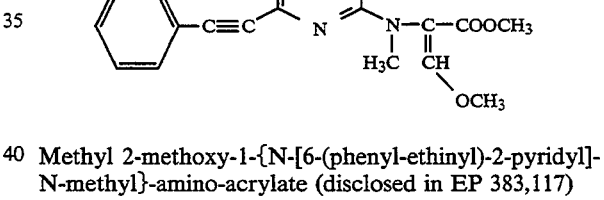

(B)

Methyl 2-methoxy-1-{N-[6-(phenyl-ethinyl)-2-pyridyl]-N-methyl}-amino-acrylate (disclosed in EP 383,117)

Example A

*Venturia* test (apple)/protective

Solvent: 4.7 parts by weight of acetone

Emulsifier: 0.3 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (*Venturia inaequalis*) and then remain in an incubation cabin at 20° C. and 100% relative atmospheric humidity for 1 day.

The plants are then placed in a greenhouse at 20° C. and a relative atmospheric humidity of about 70%.

Evaluation is carried out 12 days after inoculation.

At an active compound concentration of 5 ppm in the spraying liquid, the compound according to example (13) shows a degree of activity of more than 70%, whereas the comparison compound (B) exhibits a degree of activity of lower than 10%.

Example B

*Pyrenophora teres* test (barley)/protective
 Solvent: 100 parts by weight of dimethylformamide
 Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew moist.

After the spray coating has dried on, the plants are sprayed with a conidia suspension of *Pyrenophora teres*. The plants remain in an incubation cabin at 20° C. and 100% relative atmospheric humidity for 48 hours.

The plants are placed in a greenhouse at a temperature of about 20° C. and a relative atmospheric humidity of about 80%.

Evaluation is carried out 7 days after the inoculation.

At an active compound concentration of 250 ppm in the spraying liquid, the compounds according to examples (16), (19) and (21) show a degree of activity of more than 70%, whereas the comparison compound (A) does not exhibit any activity.

Example C

*Tetranychus* test (OP resistant)
 Solvent: 7 parts by weight of dimethylformamide
 Emulsifier: 1 part by weight of alkylaryl polyglycol ether To produce a suitable preparation of active compound, 1 part by weight of active compound is mixed with the stated amount of solvent and emulsifier, and the concentrate is diluted with emulsifier-containing water to the desired concentrations.

Bean plants (*Phaseolus vulgaris*) which are heavily infested with all developmental stages of the two spotted spider mite (*Tetranychus urticae*) are sprayed with an active compound preparation of the desired concentration until dripping wet.

After the desired time, the mortality in percent is determined. 100% means that all spider mites have been killed; 0% means that no spider mites have been killed.

At an active compound concentration of 0.1% in the spraying liquid, the compound according to example (3) shows a degree of activity of 100% after 13 days, whereas the comparison compound (A) does not exhibit any activity.

We claim:

1. Pyridyl compounds of the formula (I)

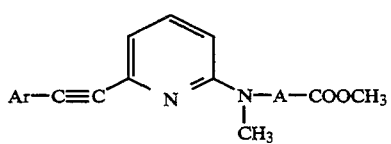

(I)

in which

Ar represents optionally substituted phenyl or optionally substituted pyridyl and A represents a CH$_2$ group or a radical of the formula

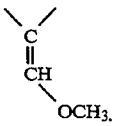

2. Pyridyl compounds of the formula (I) according to claim 1, in which

Ar represents phenyl or pyridyl, each of which is optionally monosubstituted or polysubstituted by identical or different substituents, selected from the group consisting of halogen, cyano, nitro, straight-chain or branched alkyl, alkoxy or alkylthio, each of has 1 to 4 carbon atoms, straight-chain or branched halogenoalkyl, halogenoalkoxy or halogenoalkylthio, each of which has 1 to 4 carbon atoms and 1 to 9 identical or different halogen atoms, straight-chain or branched alkoxycarbonyl or alkoximinoalkyl, each of which has 1 to 4 carbon atoms in the individual alkyl moieties, phenyl which is optionally monosubstituted or polysubstituted by identical or different substituents from the group consisting of halogen straight-chain and branched alkyl having 1 to 4 carbon atoms, and A represents a CH$_2$ group or a radical of the formula

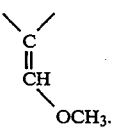

3. Compounds of the formula (I) according to claim 1, in which

Ar represents phenyl, 2-pyridyl, 3-pyridyl or 4-pyridyl, each of which is optionally monosubstituted to trisubstituted by identical or different substituents, selected from the group consisting of halogen, cyano, nitro, straight-chain or branched alkyl, alkoxy or alkylthio, each of which has 1 to 4 carbon atoms, straight-chain or branched halogenoalkyl, halogenoalkoxy or halogenoalkylthio, each of which has 1 to 4 carbon atoms and 1 to 9 identical or different halogen atoms, straight-chain or branched alkoxycarbonyl or alkoximinoalkyl, each of which has 1 to 4 carbon atoms in the individual alkyl moieties, and A represents a CH$_2$ group or a radical of the formula

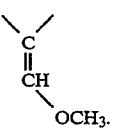

4. Compounds of the formula (I) accordingly to claim 1, in which

Ar represents phenyl, 2-pyridyl or 4-pyridyl, each of which is optionally monosubstituted or disubstituted by identical or different substituents, selected from the group consisting of fluorine, chlorine, bromine, cyano, nitro, methyl, ethyl, n- or i-propyl, n-, i-, s- and t-butyl, methoxy, ethoxy, n- and i- propoxy, n-, i-, s- and t-butoxy, methylthio, ethylthio, trifluoromethyl, trifluoromethoxy, trifluoromethylthio, methoxycarbonyl, ethoxycarbonyl, methoxyiminomethyl, methoximinoethyl, ethoximinomethyl and ethoximinoethyl, and A represents a $CH_2$ group or a radical of the formula

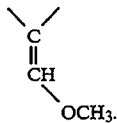

5. A pesticidal composition comprising a pesticidally effective amount of a compound according to claim 1 and a diluent.

6. A method of combating pests which comprises applying to such pests or to a pest habitat a pesticidally effective amount of a compound according to claim 1.

* * * * *

UNITED STATES PATENT AND TRADEMARK OFFICE
CERTIFICATE OF CORRECTION

PATENT NO. : 5,371,095
DATED : December 6, 1994
INVENTOR(S) : Knuppel, et al.

It is certified that error appears in the above-indentified patent and that said Letters Patent is hereby corrected as shown below:

Title Page [60] Related U.S. Application Data:
After " Ser. No. 477,271, " delete
" Jan. 8, 1990 " and substitute -- Feb. 8, 1990 --

Col. 1, line 11 Delete " Jan. 8, 1990 " and substitute -- Feb. 8, 1990 --

Signed and Sealed this

Twenty-third Day of June, 1998

Attest:

BRUCE LEHMAN

*Attesting Officer*          *Commissioner of Patents and Trademarks*